(12) United States Patent
Kumar et al.

(10) Patent No.: US 10,238,803 B2
(45) Date of Patent: *Mar. 26, 2019

(54) DRUG DELIVERY DEVICE FOR PHARMACEUTICAL COMPOSITIONS

(71) Applicant: SUN PHARMACEUTICAL INDUSTRIES LIMITED, Mumbai, Maharashtra (IN)

(72) Inventors: Ashish Kumar, Jhajjar (IN); Kalaiselvan Ramaraju, Trichirapalli (IN); Romi Barat Singh, Varanasi (IN); Bhupesh Kumar Mittal, Alwar (IN); Rahul Bhargava, New Delhi (IN); Mohit Mittal, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/853,219

(22) Filed: Dec. 22, 2017

(65) Prior Publication Data

US 2018/0133399 A1  May 17, 2018

Related U.S. Application Data

(63) Continuation-in-part of application No. 15/144,098, filed on May 2, 2016.

(51) Int. Cl.
*A61M 5/19* (2006.01)
*A61K 9/00* (2006.01)
(Continued)

(52) U.S. Cl.
CPC ............. *A61M 5/19* (2013.01); *A61K 9/0053* (2013.01); *A61K 9/5015* (2013.01);
(Continued)

(58) Field of Classification Search
CPC .. A61K 9/5015; A61K 9/0052; A61K 9/5115; A61K 9/5123; A61K 9/5161;
(Continued)

(56) References Cited

U.S. PATENT DOCUMENTS 3,156,369 A * 11/1964 Bowes ................. B65D 51/285
                                                      206/222
3,603,469 A *  9/1971 Magni ................. B65D 51/285
                                                      206/222

(Continued)

FOREIGN PATENT DOCUMENTS

CH     567 978         10/1975
EP     0 601 508 B1     3/1999
(Continued)

OTHER PUBLICATIONS

Intuiv: Highlights of prescribing information (201 X Shire US Inc, Revised Feb. 2013).

(Continued)

*Primary Examiner* — Chun Cheung
(74) *Attorney, Agent, or Firm* — Liang Frank LLP; Stanley D. Liang

(57) ABSTRACT

The present invention relates to a dual-chamber pack with a first chamber comprising a container; and a second chamber comprising a reservoir, a biphasic connector, a plunger, and a plug with a breakable polymeric membrane. The container of the first chamber is prefilled with a pharmaceutically acceptable vehicle and the reservoir of the second chamber is prefilled with a solid composition of an active ingredient, wherein the solid composition of the active ingredient is mixed with the pharmaceutically acceptable vehicle to form a liquid pharmaceutical composition upon activation of the dual-chamber pack.

5 Claims, 6 Drawing Sheets

(51) Int. Cl.
*A61K 31/155* (2006.01)
*A61K 9/51* (2006.01)
*A61K 9/50* (2006.01)
*A61K 31/43* (2006.01)
*A61M 5/315* (2006.01)
*A61M 5/24* (2006.01)
*A61M 5/50* (2006.01)

(52) U.S. Cl.
CPC .......... *A61K 9/5115* (2013.01); *A61K 9/5123* (2013.01); *A61K 9/5161* (2013.01); *A61K 31/155* (2013.01); *A61K 31/43* (2013.01); *A61M 5/2448* (2013.01); *A61M 5/2459* (2013.01); *A61M 5/315* (2013.01); *A61M 5/5086* (2013.01); *A61M 2005/2462* (2013.01)

(58) Field of Classification Search
CPC .... A61K 31/155; A61K 31/43; A61K 9/0056; A61M 5/19; A61M 5/2448; A61M 5/2459; A61M 5/315
USPC .................................................. 206/219–222
See application file for complete search history.

(56) References Cited

U.S. PATENT DOCUMENTS

| | | | |
|---|---|---|---|
| 3,632,645 A | 1/1972 | Bream et al. | |
| 3,687,076 A | 8/1972 | Friant et al. | |
| 3,840,136 A | 10/1974 | Lanfranconi et al. | |
| 3,917,063 A | 11/1975 | Chibret et al. | |
| 4,024,952 A | 5/1977 | Leitz | |
| 4,982,875 A * | 1/1991 | Pozzi | B65D 51/285 222/129 |
| 5,058,770 A | 10/1991 | Herold et al. | |
| 5,170,888 A | 12/1992 | Goncalves | |
| 5,273,760 A | 12/1993 | Oshlack et al. | |
| 5,419,445 A | 5/1995 | Kaesemeyer | |
| 5,431,915 A | 7/1995 | Harvey et al. | |
| 5,460,828 A | 10/1995 | Santus et al. | |
| 5,472,712 A | 12/1995 | Oshlack et al. | |
| 5,854,290 A | 12/1998 | Amsten et al. | |
| 5,955,106 A | 9/1999 | Moeckel et al. | |
| 6,148,996 A | 11/2000 | Morini | |
| 6,156,340 A | 12/2000 | Adeyeye et al. | |
| 6,287,599 B1 | 9/2001 | Burnside et al. | |
| 6,676,966 B1 | 1/2004 | Odidi et al. | |
| 6,811,794 B2 | 11/2004 | Burnside et al. | |
| 6,890,957 B2 | 5/2005 | Chandran et al. | |
| 7,025,200 B2 * | 4/2006 | Fontana | A61J 1/2093 206/222 |
| 7,214,387 B2 | 5/2007 | Sanghvi et al. | |
| 7,325,676 B2 * | 2/2008 | Galaz Rodriguez | B65D 51/2814 206/219 |
| 7,748,550 B2 * | 7/2010 | Cho | B65D 51/285 206/222 |
| 7,906,145 B2 | 3/2011 | Castan et al. | |
| 8,002,734 B2 | 8/2011 | Bassarab et al. | |
| 8,152,017 B2 * | 4/2012 | Lizerbram | B65D 47/243 206/219 |
| 8,197,850 B2 | 6/2012 | Castan et al. | |
| 8,215,481 B1 * | 7/2012 | Knickerbocker | B65D 51/285 206/219 |
| 8,297,456 B1 | 10/2012 | Anderson | |
| 8,318,210 B2 | 11/2012 | Tengler et al. | |
| 8,453,833 B2 | 6/2013 | Porter | |
| 8,491,935 B2 | 7/2013 | Mehta et al. | |
| 8,541,018 B2 | 9/2013 | Radke et al. | |
| 8,960,424 B1 * | 2/2015 | Anderson | B65D 51/2835 206/219 |
| 9,132,950 B1 | 9/2015 | Anderson et al. | |
| 2001/0032643 A1 | 10/2001 | Hochrainer et al. | |
| 2002/0020636 A1 * | 2/2002 | Bergamini | A61J 1/2093 206/219 |
| 2003/0171407 A1 | 9/2003 | Freese et al. | |
| 2003/0199846 A1 | 10/2003 | Fowles et al. | |
| 2004/0062800 A1 | 4/2004 | Burnside et al. | |
| 2004/0062802 A1 | 4/2004 | Hermelin | |
| 2004/0109891 A1 | 6/2004 | Sanghvi et al. | |
| 2007/0023300 A1 * | 2/2007 | Spector | B05B 11/0081 206/222 |
| 2007/0193894 A1 | 8/2007 | Macken et al. | |
| 2008/0008765 A1 | 1/2008 | Schwarz et al. | |
| 2008/0095855 A1 | 4/2008 | Shwarz | |
| 2008/0118570 A1 | 5/2008 | Liu et al. | |
| 2008/0124432 A1 | 5/2008 | Ma | |
| 2008/0202950 A1 | 8/2008 | Anderson | |
| 2008/0314775 A1 | 12/2008 | Owoc | |
| 2009/0123538 A1 | 5/2009 | Alani et al. | |
| 2009/0142378 A1 | 6/2009 | Frisbee | |
| 2009/0176691 A1 | 7/2009 | Bennis et al. | |
| 2009/0325938 A1 | 12/2009 | Lichter et al. | |
| 2010/0092562 A1 | 4/2010 | Hollenbeck et al. | |
| 2010/0282624 A1 | 11/2010 | Paganuzzi | |
| 2010/0330150 A1 | 12/2010 | enkatesh et al. | |
| 2011/0268808 A1 | 11/2011 | Jain et al. | |
| 2011/0313046 A1 | 12/2011 | Ermer | |
| 2012/0178666 A1 | 7/2012 | Franklin et al. | |
| 2012/0220930 A1 | 8/2012 | Griffiths et al. | |
| 2013/0109659 A1 | 5/2013 | Soler Ranzani et al. | |
| 2014/0050796 A1 | 2/2014 | Tengler et al. | |
| 2014/0309271 A1 | 10/2014 | Price | |
| 2014/0319141 A1 | 10/2014 | Stratis et al. | |
| 2015/0021214 A1 | 1/2015 | Besic et al. | |
| 2016/0228360 A1 | 8/2016 | Kumar et al. | |
| 2016/0228379 A1 | 8/2016 | Kumar et al. | |
| 2016/0271070 A1 | 9/2016 | Singh et al. | |
| 2016/0317388 A1 | 11/2016 | Bhargava et al. | |
| 2016/0346233 A1 | 12/2016 | Singh et al. | |
| 2016/0346235 A1 | 12/2016 | Singh et al. | |
| 2017/0119627 A1 | 1/2017 | Gambino et al. | |
| 2017/0216142 A1 | 8/2017 | Mittal et al. | |
| 2017/0304234 A1 | 10/2017 | Singh et al. | |
| 2017/0312177 A1 | 11/2017 | Bhargava et al. | |
| 2018/0133399 A1 | 5/2018 | Kumar et al. | |
| 2018/0221290 A1 | 8/2018 | Singh et al. | |
| 2018/0221314 A1 | 8/2018 | Singh et al. | |

FOREIGN PATENT DOCUMENTS

| | | |
|---|---|---|
| EP | 1 140 02 B1 | 10/2005 |
| FR | 2 897 267 A1 | 8/2017 |
| WO | WO 00/38655 | 7/2000 |
| WO | WO 2004/012715 A1 | 2/2004 |
| WO | WO 2006/030297 A1 | 3/2006 |
| WO | WO 2006/086856 A1 | 7/2008 |
| WO | WO 2008/122993 A1 | 10/2008 |
| WO | WO 2010/045656 A3 | 4/2010 |
| WO | WO 2011/077451 A3 | 6/2011 |
| WO | WO 2011/107855 A3 | 9/2011 |
| WO | WO 2011/150506 A1 | 12/2011 |
| WO | WO 2012052853 A3 | 4/2012 |
| WO | WO 2012/063257 A3 | 5/2012 |
| WO | WO 2013043064 A1 | 3/2013 |
| WO | WO 2013091882 A1 | 6/2013 |
| WO | WO 2014/174119 A1 | 10/2014 |
| WO | WO 2015 166472 A1 | 11/2015 |
| WO | WO 2015 166473 A1 | 11/2015 |
| WO | WO 2015 166473 A1 | 11/2015 |
| WO | WO 2016/016845 A1 | 2/2016 |
| WO | WO 2016 178130 A1 | 11/2016 |
| WO | WO 2016 178131 A1 | 11/2016 |
| WO | WO 2016 178132 A1 | 11/2016 |
| WO | WO 2017 182851 A1 | 10/2017 |
| WO | WO 2017 182852 A1 | 10/2017 |
| WO | WO 2017 191485 A1 | 11/2017 |

OTHER PUBLICATIONS

Kristine, "EKG Results/Tenex", Dr. Mom's Spot (Mar. 26, 2010) Available: http://drmomsspot.blogspot.com/2010/03/ekg-results-

(56) References Cited

OTHER PUBLICATIONS tenex.html (Accessed on: Unknown—Examiner does not provide date on PTO-892 form nor is it listed on the art).
Lopez-Liuchi et al., "Therapy for type 2 diabetes: where do we stand after the UK Prospective Diabetes Study?," European Journal of Endocrinology, 140:4-6 (1999).
Murtaza,"Ethylcellulose Microparticles: A Review," Drug Research, 69(1):11-22 (2012).
Steeman, 2009. Innovative dispensing bottle caps for sensitive vitamins [online]. Best in Packaging. Available from: http://bestinpackaging.com/2009/05/29/innovative-dispensing-bottle-caps-for-sensitive-vitamins/.
Medela Breast Milk Bottle Set, Target, published on or before 2010. Available from: www.target.com/p/medela-breast-milk-set-8oz-3ct/-/A-11189915 (Accessed on: Aug. 14, 2017).
International Search Report and Written Opinion for International Application No. PCT/IB2015/053207, issued by US/ISA dated Aug. 2017.
International Preliminary Report on Patentability for International Application No. PCT/IB2015/053207, issued by WIPO dated Mar. 16, 2016.
Restriction Requirement for U.S. Appl. No. 15/133,773, issued by USPTO dated Jun. 10, 2016.
Office Action for U.S. Appl. No. 15/133,773, issued by USPTO dated Jul. 27, 2016.
Final Office Action for U.S. Appl. No. 15/133,773, issued by USPTO dated Dec. 16, 2016.
Final Office Action for U.S. Appl. No. 15/133,773, issued by USPTO dated Apr. 13, 2017.
International Search Report and Written Opinion for International Application No. PCT/IB2016/052484, issued by US/ISA dated Sep. 8, 2016.
Final Office Action for U.S. Appl. No. 15/144,000, issued by USPTO dated Nov. 4, 2016.
Office Action for U.S. Appl. No. 15/144,000, issued by USPTO dated Feb. 14, 2017.
International Search Report and Written Opinion for International Application No. PCT/IB2015/053209, issued by US/ISA dated Aug. 14, 2015.
International Preliminary Report on Patentability for International Application No. PCT/IB2015/053209, issued by WIPO dated Nov. 10, 2016.
Restriction Requirement for U.S. Appl. No. 15/133,826, issued by USPTO dated Jun. 23, 2016.
Office Action for U.S. Appl. No. 15/133,826, issued by USPTO dated Jul. 28, 2016.
Final Office Action for U.S. Appl. No. 15/133,826, issued by USPTO dated Dec. 20, 2016.
Office Action for U.S. Appl. No. 15/133,826, issued by USPTO dated Feb. 14, 2017.
Restriction Requirement for U.S. Appl. No. 15/148,069, issued by USPTO dated Jul. 21, 2016.
Office Action for U.S. Appl. No. 15/148,069, issued by USPTO dated Nov. 2, 2016.
Final Office Action for U.S. Appl. No. 15/148,069, issued by USPTO dated Mar. 20, 2017.
Office Action for U.S. Appl. No. 15/148,131, issued by USPTO dated Oct. 7, 2016.
Final Office Action for U.S. Appl. No. 15/148,131, issued by USPTO dated Apr. 5, 2017.
International Search Report and Written Opinion for International Application No. PCT/IB2016/052485, issued by US/ISA dated Aug. 31, 2016.
Office Action for U.S. Appl. No. 15/144,026, issued by USPTO dated Oct. 12, 2016.
Final Office Action for U.S. Appl. No. 15/144,026, issued by USPTO dated Apr. 6, 2017.
International Search Report and Written Opinion for International Application No. PCT/IB2015/055780, issued by US/ISA dated Dec. 7, 2015.
International Preliminary Report on Patentability for International Application No. PCT/IB2015/055780, issued by WIPO dated Feb. 9, 2017.
International Search Report and Written Opinion for International Application No. PCT/IB2016/052486, issued by US/ISA on Sep. 9, 2016.
Restriction Requirement for U.S. Appl. No. 15/144,058, issued by USPTO dated Sep. 30, 2016.
Office Action for U.S. Appl. No. 15/144,058, issued by USPTO dated Dec. 16, 2016.
Office Action for U.S. Appl. No. 15/144,058, issued by USPTO dated May 11, 2017.
Final Office Action for U.S. Appl. No. 15/144,058, issued by USPTO dated Jul. 21, 2017.
Office Action for U.S. Appl. No. 15/352,993, issued by USPTO dated Mar. 24, 2017.
International Search Report and Written Opinion for International Application No. PCT/IB2016/025488, issued by US/ISA dated Aug. 31, 2016.
Office Action for U.S. Appl. No. 15/144,098, issued by USPTO dated Jul. 13, 2017.
Office Action for U.S. Appl. 15/133,773, issued by USPTO dated Aug. 1, 2017.
Office Action for U.S. Appl. No. 15/148,069, issued by USPTO dated Aug. 10, 2017.
Office Action for U.S. Appl. No. 15/144,026, issued by USPTO dated Aug. 24, 2017.
Office Action for U.S. Appl. No. 15/352,993, issued by USPTO dated Aug. 24, 2017.
Final Office Action for U.S. Appl. No. 15/144,000, issued by USPTO dated Aug. 24, 2017.
Office Action for U.S. Appl. No. 15/148,131, issued by USPTO dated Sep. 29, 2017.
Office Action for U.S. Appl. No. 15/329,070, issued by USPTO dated Nov. 21, 2017.
International Preliminary Report on Patentability for International Application No. PCT/IB2016/052485, issued by WIPO dated Nov. 16, 2016
International Preliminary Report on Patentability for International Application No. PCT/IB2016/052484, issued by WIPO dated Nov. 16, 2017.
International Preliminary Report on Patentability for International Application No. PCT/IB2016/052486, issued by WIPO dated Nov. 16, 2017.
Final Office Action for U.S. Appl. No. 15/133,773, issued by USPTO dated Dec. 11, 2017.
Office Action for U.S. Appl. No. 15/144,058, issued by USPTO dated Jan. 16, 2018.
Final Office Action for U.S. Appl. No. 15/148,069, issued by USPTO dated Jan. 19, 2018.
Final Office Action for U.S. Appl. No. 15/352,993, issued by USPTO dated Feb. 8, 2018.
Final Office Action for U.S. Appl. No. 15/144,026, issued by USPTO dated Feb. 7, 2018.
Final Office Action for U.S. Appl. No. 15/133,826, issued by USPTO dated Feb. 12, 2018.
Final Office Action for U.S. Appl. No. 15/144,098, issued by USPTO dated Feb. 22, 2018.
Office Action for U.S. Appl. No. 15/144,000, issued by USPTO dated Mar. 14, 2018.
Office Action for U.S. Appl. No. 15/148,131, issued by USPTO dated Apr. 6, 2018.
Office Action for U.S. Appl. No. 15/942,840, issued by USPTO dated May 29, 2018.
Restriction Requirement for U.S. Appl. No. 15/800,682, issued by USPTO dated Dec. 15, 2017.
Timmins et al, "Steady-State Pharmacokinet of a Novel Extended-Release Metformin Formulation", Clinical Pharmacokinet., 44(7):721-729 (2005).

(56) References Cited

OTHER PUBLICATIONS

Office Action for AU Application No. 2017279809, issued by AU PTO dated Jun. 1, 2018.
Office Action for AU Application No. 2017254908, issued by AU PTO dated Jun. 1, 2018.
Final Office Action for U.S. Appl. No. 15/329,070, issued by USPTO dated Jun. 11, 2018.
Office Action for U.S. Appl. No. 15/942,711, issued by USPTO dated Jun. 20, 2018.
Final Office Action for U.S. Appl. No. 15/148,131, issued by USPTO dated Aug. 6, 2018.
European Extended Search Report dated Jun. 6, 2018 for European Patent Application No. 17210326.9.
Office Action for U.S. Appl. No. 15/144,000, issued by USPTO dated Aug. 31, 2018.
Office Action for U.S. Appl. No. 15/800,682, issued by USPTO dated Apr. 10, 2018.

* cited by examiner

Top view    Front view

DRUG DELIVERY DEVICE FOR PHARMACEUTICAL COMPOSITIONS

REFERENCE TO RELATED APPLICATIONS

In accordance with 37 C.F.R. § 1.76, a claim of priority is included in an Application Data Sheet filed concurrently with the present application. Accordingly, the present invention claims priority under 35 U.S.C. §§ 119(e), 120, 121, and/or 365(c) to U.S. patent application Ser. No. 15/144,098, entitled "DUAL-CHAMBER PACK FOR PHARMACEUTICAL COMPOSITIONS," filed on May 2, 2016, of which the present application is a continuation-in-part. The content of the above-referenced application is incorporated herein by reference in its entirety.

FIELD OF THE INVENTION

The present invention relates to a dual-chamber pack with a first chamber comprising a container; and a second chamber comprising a reservoir, a biphasic connector, a plunger, and a plug with a breakable polymeric membrane. The container of the first chamber is prefilled with a pharmaceutically acceptable vehicle and the reservoir of the second chamber is prefilled with a solid composition of an active ingredient, wherein the solid composition of the active ingredient is mixed with the pharmaceutically acceptable vehicle to form a liquid pharmaceutical composition upon activation of the dual-chamber pack.

BACKGROUND OF THE INVENTION

Liquid pharmaceutical compositions are convenient dosage forms for oral administration particularly for geriatric and pediatric patients in comparison to solid dosage forms such as tablets and capsules. They are easy to administer which leads to enhanced patient compliance. Additionally, liquid pharmaceutical compositions provide a unique advantage of having a flexible dosing regimen. Liquid pharmaceutical compositions are also preferred over solid dosage forms in case of high-dose drugs considering the size and shape requirements imposed by various regulatory authorities worldwide and the swallowability of the dosage form. Liquid pharmaceutical compositions are generally in the form of a solution, emulsion or a suspension, wherein the active ingredient remains in the dissolved or dispersed form in a pharmaceutically acceptable vehicle such as water.

However, some of the active ingredients remain unstable in the presence of pharmaceutically acceptable vehicle such as water when stored for a prolonged period of time. To overcome this, the active ingredients are mostly formulated as a dry powder which is to be reconstituted with the pharmaceutically acceptable vehicle at the time of administration. The reconstitution is done by the end user, wherein the dry powder is dissolved or suspended in a household pre-boiled and cooled water to form a liquid pharmaceutical composition. Alternatively, the pharmaceutically acceptable vehicle or purified water is supplied separately along with the bottle having the dry powder. This conventional pack lacks patient compliance and may lead to contamination due to improper quality of water. Further, there remains a possibility of dosing errors if the pharmaceutically acceptable vehicle or water is not added to the marked level.

U.S. Pat. No. 3,156,369; U.S. Pat. No. 3,603,469; U.S. Pat. No. 3,840,136; and U.S. Pat. No. 4,982,875 disclose the use of dual-chamber packs for separately storing two compositions in two compartments which can be admixed at the time of use. The two compartments are separated by a breakable membrane which is ruptured by the depression of a plunger so that the one composition gets released into another and is mixed. However, there remains a possibility that the membrane fragments may get detached and fall into the final product. This may lead to undesirable contamination and can pose serious health hazards. Furthermore, the dual-chamber packs disclosed in the prior art have a limited capacity for the compartments which may not be suitable for high-dose drugs or for drugs which require chronic administration. Also, the liquid composition may get permeated into the solid composition across the membrane during storage which can lead to the agglomeration of the solid composition. This may result in poor flow of the solid composition, thus affecting the content uniformity of the final product. Also, the liquid composition on permeation can affect the stability of moisture-sensitive drugs.

The present invention provides a patient compliant dual-chamber pack with a significant improvement over the prior art and which fulfills the unmet need of incorporating variety of drugs. The present dual-chamber pack can be suitable for any class of drugs including the high-dose drugs, drugs requiring chronic administration, or moisture-sensitive drugs. Multi-dose liquid compositions can be conveniently administered using this pack. Further, the plunger used in the pack of the instant invention is designed in a way such that the breakable membrane remains adhered to the plug at the time of activation and membrane fragments do not fall into the final product. During activation, the pack ensures that the final product remains safe for the use of patients. The pack also ensures that the solid composition is completely released into the liquid composition thereby maintaining the content uniformity of the final product. Further, the pack also ensures that there is no permeation of moisture into the chamber having solid composition comprising the active ingredient, and the stability of the active ingredient remains unaffected during storage.

SUMMARY OF THE INVENTION

The present invention relates to a dual-chamber pack with a first chamber comprising a container; and a second chamber comprising a reservoir, a biphasic connector, a plunger, and a plug with a breakable polymeric membrane. The container of the first chamber is prefilled with a pharmaceutically acceptable vehicle and the reservoir of the second chamber is prefilled with a solid composition of an active ingredient, wherein the solid composition of the active ingredient is mixed with the pharmaceutically acceptable vehicle to form a liquid pharmaceutical composition upon activation of the dual-chamber pack. The pack allows the end-users ease of dispensing with only a few simple steps required for reconstitution. The pack is suitable for drugs required for chronic administration, high-dose drugs, and moisture-sensitive drugs. The pack ensures that the solid composition falls completely into the pharmaceutically acceptable vehicle thereby maintaining the content uniformity. The pack also ensures that final product remains free of any contamination from the pack components and is safe to the end-users. Further, the pack ensures the stability of the active ingredient during storage.

DETAILED DESCRIPTION OF THE INVENTION

Figure 1:
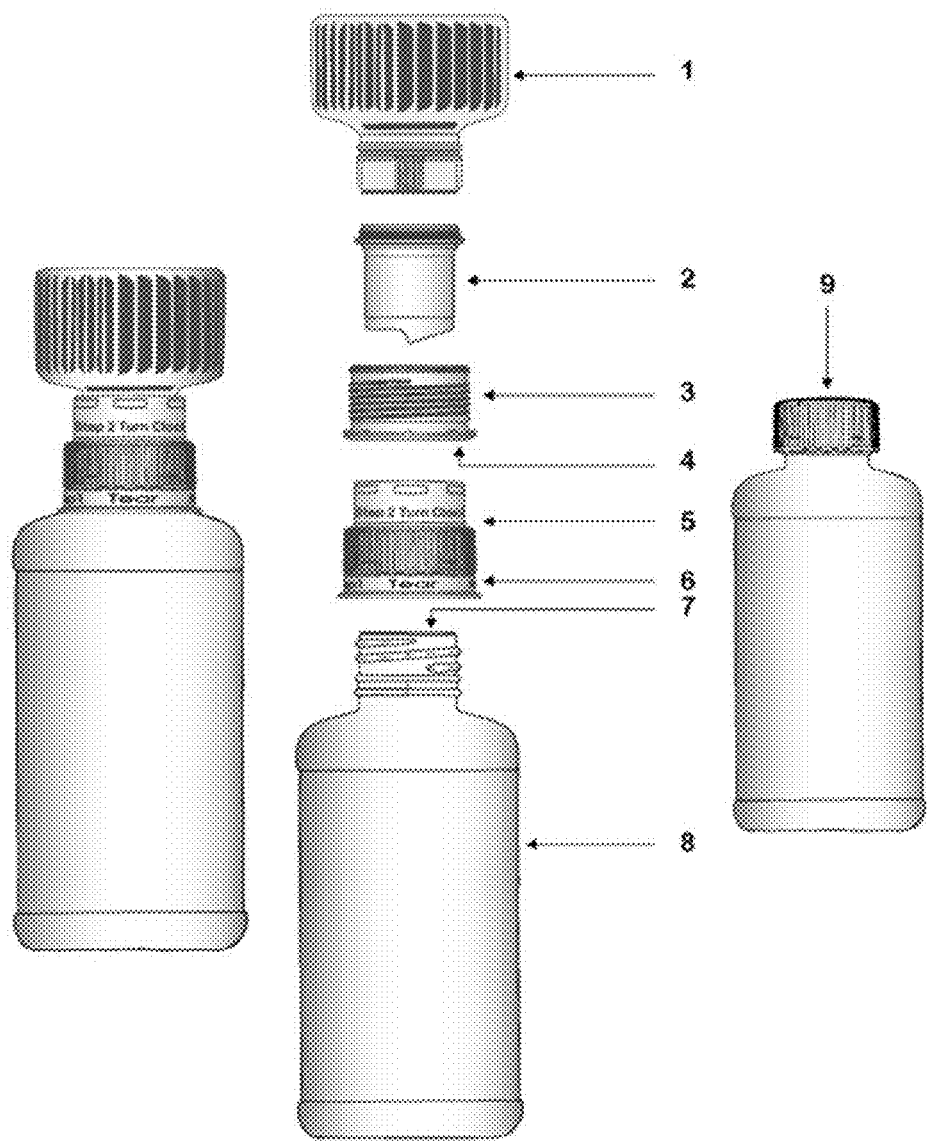
FIG. 1: Schematic diagram of the components of a dual-chamber pack comprising the following: Reservoir—1, Plunger—2, Plug—3, Breakable polymeric membrane—4, Biphasic connector—5, Tamper evident band—6, Opening of the container—7, Container—8, Cap—9.
Figure 2:
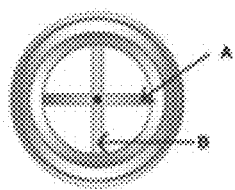
FIG. 2: Schematic diagram for the biphasic connector—top view and front view: Tapered design for no product retention—A, Cross-sectional ribs for imparting strength to the component—B, Locking mechanism—C, Tamper evident band—D.
Figure 2:
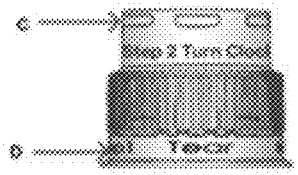
Figure 3:
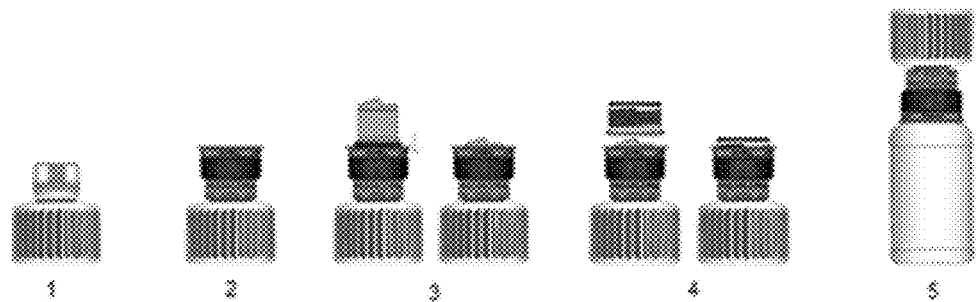
FIG. 3: Schematic diagram representing the assembly of a dual-chamber pack.
1. Prefilling the reservoir with a solid composition.
2. Outer shell of biphasic connector is affixed with the reservoir.
3. Plunger is placed inside the biphasic connector.
4. Plunger is fixed with the biphasic connector to complete the second chamber.
5. Second chamber is inverted and placed over the container of the first chamber prefilled with pharmaceutically acceptable vehicle.
Figure 4:
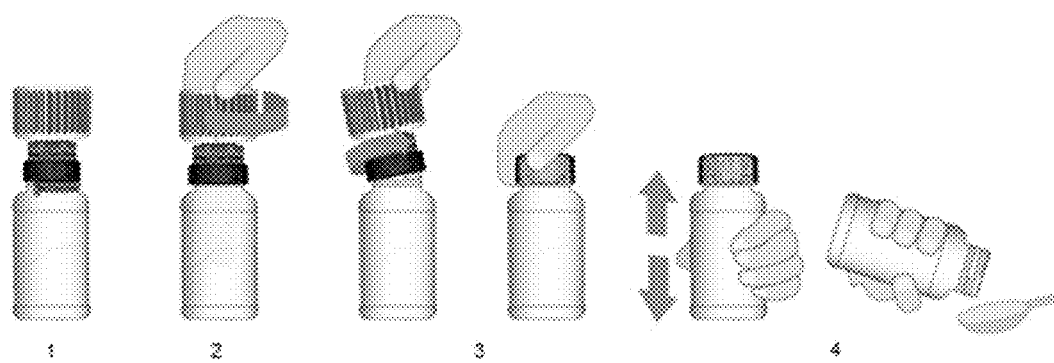
FIG. 4: Schematic diagram representing the functioning of a dual-chamber pack
1. Remove the tear band.
2. Screw the top chamber clockwise to break the polymeric membrane in the plug, which makes the solid composition fall into the container of the first chamber prefilled with pharmaceutically acceptable vehicle.
3. Remove the second chamber from the neck of the container of the first chamber and replace it with a child-resistant cap.
4. Shake well to mix before administration.
Figure 5:
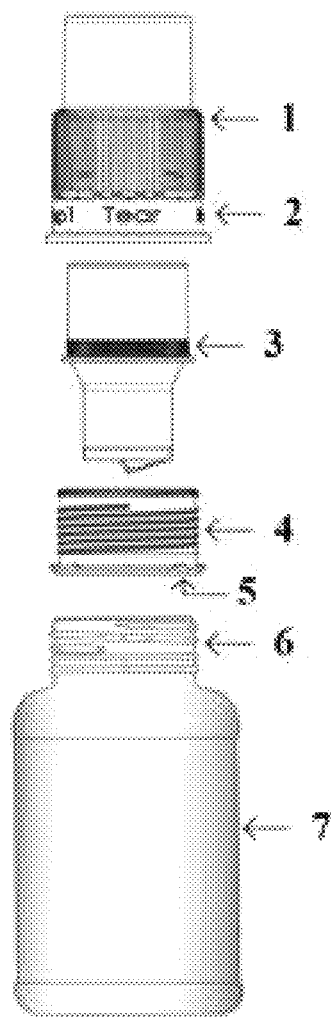
FIG. 5: Schematic diagram of the components of a drug delivery device: Cap—1, Tamper evident band—2, Plunger—3, Plug—4, Breakable substantially impermeable membrane—5, Opening of the container—6, Container—7.
Figure 6:
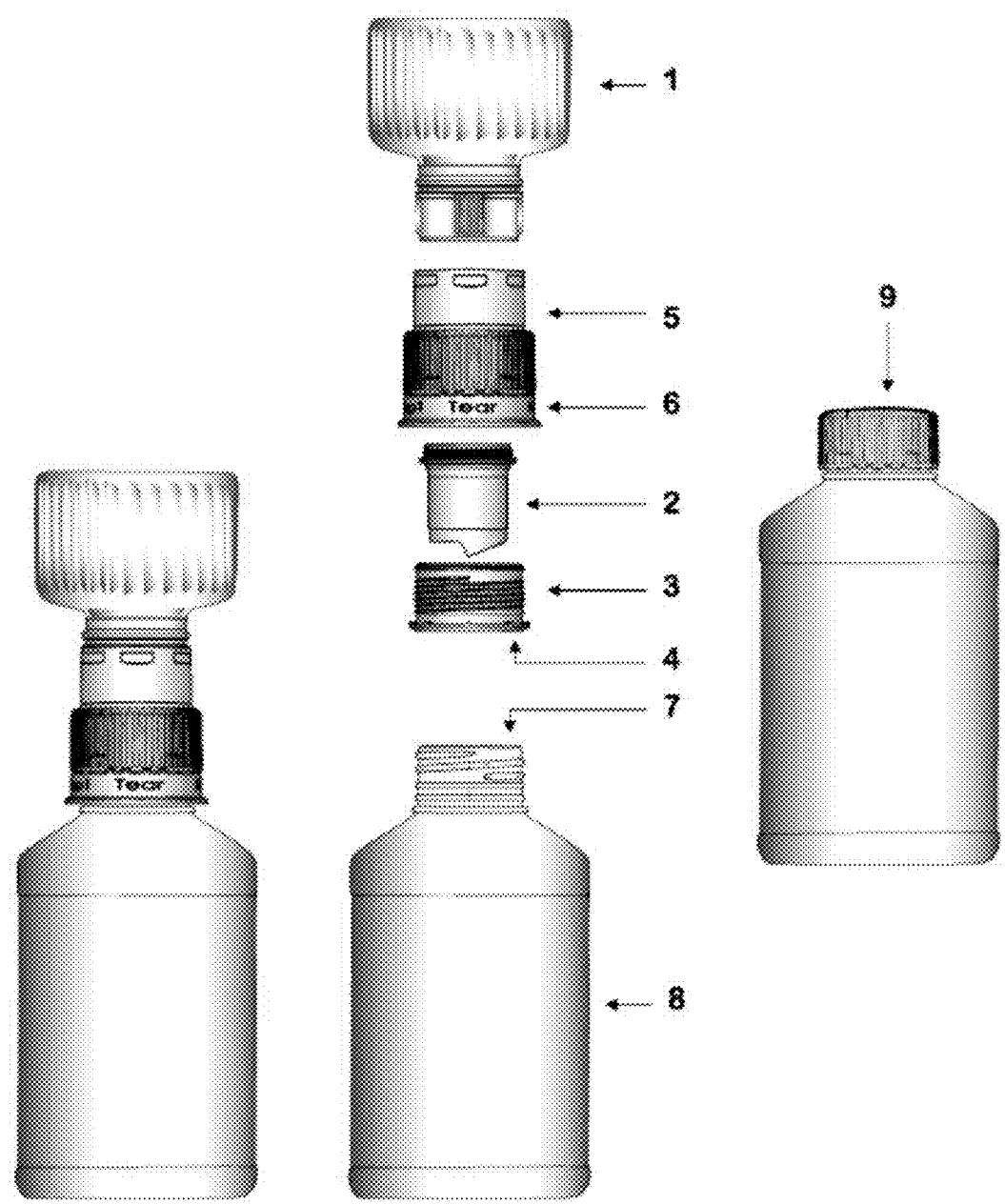
FIG. 6: Schematic diagram of the components of a dual-chamber pack with a powder for suspension filled in the reservoir. Reservoir—1, Plunger—2, Plug—3, Breakable polymeric membrane—4, Biphasic connector—5, Tamper evident band—6, Opening of the container—7, Container—8, Cap—9.

A first aspect of the invention provides a dual-chamber pack comprising:
(a) a first chamber comprising a container; and
(b) a second chamber comprising a reservoir, a biphasic connector, a plunger, and a plug with a breakable polymeric membrane.

According to one embodiment of the above aspect, the container of the first chamber is prefilled with a pharmaceutically acceptable vehicle and the reservoir of the second chamber is prefilled with a solid composition of an active ingredient. Alternatively, the reservoir of the second chamber is prefilled with a liquid concentrate composition of an active ingredient.

According to another embodiment of the above aspect, the solid composition is mixed with the pharmaceutically acceptable vehicle to form a liquid pharmaceutical composition upon activation of the dual-chamber pack.

According to another embodiment of the above aspect, the liquid pharmaceutical composition is a solution or a suspension.

According to another embodiment of the above aspect, the dual chamber pack is used for multi-dose administration of the liquid pharmaceutical composition.

According to another embodiment of the above aspect, the reservoir of the second chamber is prefilled with the solid composition in a volume greater than about 40 cc. In a preferred embodiment of above aspect, the reservoir of the second chamber is prefilled with the solid composition in a volume ranging from about 40 cc to about 500 cc.

According to another embodiment of the above aspect, the biphasic connector of the second chamber connects the reservoir to the container of the first chamber.

According to another embodiment of the above aspect, the plunger ensures the breakable polymeric membrane remains attached to the plug during activation.

According to another embodiment of the above aspect, the plunger comprise of one or more sharp projections with an essential continuous blunt area. In a preferred embodiment, the plunger comprise of one sharp projection with an essential continuous blunt area. The plunger can further have one or more grooves. The body of the plunger can be in the form of a cylinder or a funnel.

According to another embodiment of the above aspect, the plug is made up of polymeric materials selected from the group comprising polyolefin, polyethylene, polypropylene, polyvinyl chloride, cyclic olefin polymer, cyclic olefin co-polymer, polyethylene terephthalate, polyethylene terephthalate-G, polypropylene, and polycarbonate. In a preferred embodiment, the plug is made up of polyethylene.

According to another embodiment of the above aspect, the plug additionally includes one or more moisture barrier additives.

According to another embodiment of the above aspect, the moisture barrier additives are selected from the plastic additive group comprising of monomers and co-polymers that get activated through polymerization process to form an effective organic chemical.

According to another embodiment of the above aspect, the moisture barrier additives improve the moisture barrier properties by up to 50%. In particular, the moisture barrier additives improve the moisture barrier properties by up to 30%.

According to another embodiment of the above aspect, the plug with the breakable polymeric membrane prevents moisture permeation from the first chamber into the second chamber.

According to another embodiment of the above aspect, the liquid pharmaceutical composition is a stable composition.

According to another embodiment of the above aspect, the liquid pharmaceutical composition is a taste-masked composition.

A second aspect of the present invention provides a dual-chamber pack comprising:
a) a first chamber in the form of a container (8) prefilled with a pharmaceutically acceptable vehicle provided with an opening (7) at an upper end;
b) a second chamber comprising:
(i) a reservoir (1) adapted to fit into a plunger (2) prefilled with a solid composition of an active ingredient; the plunger (2) is further adapted to fit into a plug (3) having a top flat surface,
(ii) the plug (3), with a breakable polymeric membrane (4), adapted to fit into the biphasic connector (5) optionally having a tamper evident band (6) which is further connected from the lower end to the opening (7) of the container (8);
wherein the reservoir (1) at the top of the second chamber has a means to exert pressure onto the plunger (2) so as to partially rupture the breakable polymeric membrane (4) of the plug and deliver the solid composition into the pharmaceutically acceptable vehicle of the container (8); the second chamber is replaced with a cap (9), and wherein the solid composition is mixed with the pharmaceutically acceptable vehicle to form a liquid pharmaceutical composition.

According to one embodiment of the above aspect, the reservoir of the second chamber is prefilled with the solid composition in a volume greater than about 40 cc. In a preferred embodiment of above aspect, the reservoir of the second chamber is prefilled with the solid composition in a volume ranging from about 40 cc to about 500 cc.

According to another embodiment of the above aspect, the cap is a conventional cap or a child-resistant cap.

According to another embodiment of the above aspect, the biphasic connector has a tamper evident band on the side connected to the container of the first chamber and grooves on another side for locking with the reservoir of the second chamber.

According to another embodiment of the above aspect, the plunger is opened at both the ends.

According to another embodiment of the above aspect, the reservoir exerts pressure onto the plunger when it is screwed during the activation of the dual-chamber pack.

A third aspect of the present invention provides a method of providing a liquid pharmaceutical composition stored in a dual-chamber pack, comprising the steps of:
  (a) providing a first chamber comprising a container (8), a second chamber comprising a reservoir (1), a plunger (2), a plug (3) with a breakable polymeric membrane (4), and a biphasic connector (5);
  (b) prefilling the container (8) of the first chamber with a pharmaceutically acceptable vehicle to form a first chamber;
  (c) prefilling a reservoir (1) of the second chamber with a solid composition;
  (d) fixing the biphasic connector (5) into the reservoir (1);
  (e) fixing the plunger (2) in the biphasic connector (5);
  (f) mounting the plug (3) onto the plunger of the biphasic connector (5) to form the second chamber;
  (g) mounting the second chamber onto the opening (7) of the container (8) of the first chamber;
  (h) activating the dual-chamber pack by screwing the reservoir (1) of the second chamber so that the plunger partially ruptures the circumference of a breakable polymeric membrane; and
  (i) removing the second chamber and replacing it with a cap (9); and
  (j) shaking the container (8) to allow the mixing of the solid composition with the pharmaceutically acceptable vehicle to obtain the liquid pharmaceutical composition.

According to one embodiment of the above aspect, the reservoir of the second chamber is prefilled with the solid composition in a volume greater than about 40 cc. In a preferred embodiment of above aspect, the reservoir of the second chamber is prefilled with the solid composition in a volume ranging from about 40 cc to about 500 cc.

According to another embodiment of above aspect, the biphasic connector has a tamper evident band on the side connected to the container of the first chamber and grooves on another side for locking with the reservoir of the second chamber. The tamper evident band is removed first to start the activation process.

The active ingredient used to form a solid composition of the present invention may be present in a form to provide an immediate release, delayed release or an extended release. The solid composition may comprise of an active ingredient directly mixed with one or more pharmaceutically acceptable excipients. Alternatively, the solid composition may comprise of cores of an active ingredient, optionally admixed with one or more pharmaceutically acceptable excipients. The cores may be coated with an immediate release or an extended release coating. The immediate release coating may comprise a film-forming agent to mask the taste of bitter active ingredients or to improve the stability. Said coating remains insoluble in the reconstituted liquid pharmaceutical composition during storage and releases the active ingredient only once ingested. The film-forming agent can be a water-soluble polymer in which the release of active ingredient is prevented by using a high molar concentration of the solutes in the reconstituted composition, wherein the solutes have a higher affinity towards water. The high molar concentration of the solutes generates hypertonic conditions leading to high osmolality and thus prevents the leaching of the active ingredient from the coated cores. This would help to mask the taste of the bitter active ingredients or to improve the stability of active ingredients. Further, the film-forming agent can be having a pH-dependent solubility in which the release of active ingredient is prevented by using a pre-adjusted pH of the reconstituted composition such that the film-forming agent does not get dissolved in the reconstituted composition but get dissolved when exposed to the physiological conditions. Alternatively, the solid composition comprises of active ingredient in a complexed form such as ion-exchange resin complex or a cyclodextrin complex, optionally admixed with one or more pharmaceutically acceptable excipients. In this case, the active ingredient is released when exposed to the physiological conditions upon ingestion. The extended release coating may comprise of a pH-dependent release-controlling agent, a pH-independent release-controlling agent, or mixtures thereof.

Suitable examples of pH-dependent release-controlling agents are selected from the group comprising acrylic copolymers such as methacrylic acid and methyl methacrylate copolymers, e.g., Eudragit® L 100 and Eudragit® S 100, methacrylic acid and ethyl acrylate copolymers, e.g., Eudragit® L 100-55 and Eudragit® L 30 D-55, dimethylaminoethyl methacrylate and butyl methacrylate and methyl methacrylate copolymers e.g., Eudragit® E 100, Eudragit® E PO, methyl acrylate and methacrylic acid and octyl acrylate copolymers, styrene and acrylic acid copolymers, butyl acrylate and styrene and acrylic acid copolymers, and ethylacrylate-methacrylic acid copolymer; cellulose acetate phthalate; cellulose acetate succinates; hydroxyalkyl cellulose phthalates such as hydroxypropylmethyl cellulose phthalate; hydroxyalkyl cellulose acetate succinates such as hydroxypropylmethyl cellulose acetate succinate; vinyl acetate phthalates; vinyl acetate succinate; cellulose acetate trimelliate; polyvinyl derivatives such as polyvinyl acetate phthalate, polyvinyl alcohol phthalate, polyvinyl butylate phthalate, and polyvinyl acetoacetal phthalate; zein; shellac; and mixtures thereof.

Suitable examples of pH-independent release-controlling agents are selected from the group comprising cellulosic polymers such as ethyl cellulose, methyl cellulose, hydroxyethyl cellulose, hydroxypropyl cellulose, hydroxyethylmethyl cellulose, hydroxypropylmethyl cellulose, and carboxy methylcellulose; acrylic copolymers such as methacrylic acid copolymers, e.g., Eudragit® RS, Eudragit® RL, Eudragit® NE 30 D; cellulose acetate; polyethylene derivatives e.g., polyethylene glycol and polyethylene oxide; polyvinyl alcohol; polyvinyl acetate; gums e.g., guar gum, locust bean gum, tragacanth, carrageenan, alginic acid, gum acacia, gum arabic, gellan gum, and xanthan gum; triglycerides; waxes, e.g., Compritol®, Lubritab®, and Gelucires®; lipids; fatty acids or their salts/derivatives; a mixture of polyvinyl acetate and polyvinyl pyrrolidone, e.g., Kollidon® SR; and mixtures thereof.

The term "liquid concentrate composition," as used herein refers to a concentrated liquid composition comprising an active ingredient which upon reconstitution gives the desired strength.

According to another embodiment of the above aspects, the core is in the form of a bead, a pellet, a granule, a spheroid, or the like.

According to another embodiment of the above aspects, the active ingredient is layered onto an inert particle to form the core.

A fourth aspect of the present invention provides a drug delivery device for the in situ preparation of an extended release oral suspension upon activation of the device, the device comprising:
  a) a first chamber comprising a suspension base;
  b) a second chamber comprising a solid composition comprising cores of active ingredient coated with a release controlling agent to form coated cores; and
  c) a breakable substantially impermeable polymeric membrane separating the first and second chambers,
wherein the solid composition remains stable when stored at 40° C./75% RH for at least three months.

According to one embodiment of the above aspect, the breakable substantially impermeable polymeric membrane has moisture vapor transmission rate less than about 5.0 g/m$^2$/day. More preferably, the breakable substantially impermeable polymeric membrane has moisture vapor transmission rate less than about 1.0 g/m$^2$/day.

According to another embodiment of the above aspect, the breakable substantially impermeable polymeric membrane prevents intimate contact between the contents of first and second chamber before activation.

According to another embodiment of the above aspect, the device ensures free flow of the coated cores from second chamber to first chamber upon activation of the device.

According to another embodiment of the above aspect, the breakable substantially impermeable polymeric membrane is made up of a polymeric material selected from the group consisting of polyethylene (PE), low density polyethylene (LDPE), linear low density polyethylene (LLDPE), high density polyethylene (HDPE) and high barrier grade PE.

According to another embodiment of the above aspect, the breakable substantially impermeable polymeric membrane has a thickness not less than 0.10 mm.

According to another embodiment of the above aspect, the second chamber comprises a plunger for storing the solid composition and a plug fitted with a breakable substantially impermeable polymeric membrane.

According to another embodiment of the above aspect, the solid composition prefilled in the second chamber is present in a volume ranging from about 0.5 cc to about 40 cc.

According to another embodiment of the above aspect, the first chamber comprises a container and the second chamber comprises an overcap, a plunger, and a plug with a breakable substantially impermeable polymeric membrane. The plunger is prefilled with the solid composition in a volume ranging from about 0.5 cc to about 40 cc.

According to another embodiment of the above aspect, after activation of the device, not more than about 50% of the circumference of the breakable substantially impermeable polymeric membrane remains attached to the plug to allow free flow of the coated cores from second chamber to first chamber. Preferably, after activation of the device, not more than about 30% of the circumference of the breakable substantially impermeable polymeric membrane remains attached to the plug to allow free flow of the coated cores from second chamber to first chamber. More preferably, after activation of the device, not more than about 15% of the circumference of the breakable substantially impermeable polymeric membrane remains attached to the plug to allow free flow of the coated cores from second chamber to first chamber.

According to another embodiment of the above aspect, the plunger comprises one or more sharp projections with an essential continuous blunt area at an angle of not more than about 60°.

According to another embodiment of the above aspect, the drug delivery device comprises:
  (a) a first chamber in the form of a container (7) provided with an opening (6) at an upper end, comprising a suspension base containing one or more pharmaceutically acceptable inert excipients;
  (b) a second chamber comprising:
    (i) a plunger (3) adapted to fit into a plug (4) having a top flat surface, containing a solid composition comprising cores of active ingredient coated with a release controlling agent to form coated cores; and
    (ii) the plug (4), with a breakable substantially impermeable polymeric membrane (5), adapted to fit into the opening (6) from a lower end and into a cap (1) from the upper end; and
  (c) the cap (1) over the second chamber comprising a means to exert pressure onto the plunger (3) so as to partially rupture the breakable substantially impermeable polymeric membrane (5) of the plug (4) and deliver the solid composition into the container (7)
wherein the compositions of both chambers are mixed at the time of first administration by applying pressure on the cap (1) to in situ form an extended release oral liquid suspension.

A fifth aspect of the present invention provides an extended release reconstituted powder for suspension composition comprising:
  a) cores comprising an active ingredient selected from group consisting of a high-dose, a low-dose, a water-soluble and a water-insoluble active ingredient; and
  b) a coating layer over the core comprising not more than one functional coating layer comprising a pH-independent release-controlling agent to form the coated cores
wherein the composition after reconstitution does not settle and exhibit a sedimentation volume of about 1 after about at least twelve hours after reconstitution.

According to one embodiment of the above aspects, the composition after reconstitution does not settle after about at least one month.

According to another embodiment of the above aspects, the coated cores exhibit an angle of repose less than about 40°.

According to another embodiment of the above aspects, the coated cores exhibit desired flowability.

According to another embodiment of the above aspects, the coated cores exhibit a sphericity (SPHT$_3$) value more than about 0.7 when measured using CamSizer particle analyzer from Retsch Technology.

According to another embodiment of the above aspects, the composition is characterized by having water activity of suspension base sufficiently low to prevent growth of *Burkholderia cepacia* complex.

According to another embodiment of the above aspects, the composition is characterized by having water activity of suspension base of less than about 0.9. Preferably, the composition is characterized by having water activity of suspension base of about 0.88. Water activity was determined by Rotronic hygropalm.

According to another embodiment of the above aspects, the composition provides uniform dose of the active ingredient and has a viscosity ranging from about 500 cps to about 15,000 cps. Preferably, the viscosity of the composition ranges from about 1,000 cps to about 13,000 cps. More preferably, the viscosity of the composition ranges from about 1300 cps to about 12,000 cps. The viscosity of the composition of the present invention is measured by using a Brookfield Viscometer.

A sixth aspect of the present invention provides an extended release powder for suspension composition of active ingredient comprising cores of active ingredient coated with a release-controlling agent to form coated cores, wherein the coated cores upon reconstitution with the suspension base form a suspension which is characterized by having no significant leaching of active ingredients from the extended release coated cores when placed in a medium having a pH ranging from about 1.5 to about 10.

A seventh aspect of the present invention provides a drug delivery device for the in situ preparation of an immediate release oral liquid composition upon activation of the device, the device comprising:
a) a first chamber comprising a vehicle;
b) a second chamber comprising a solid composition; and
c) a breakable substantially impermeable polymeric membrane separating first and second chamber
wherein solid composition is in the form of an immediate release powder.

The dual chamber pack of the present invention is suitable for multi-dose administration of the active ingredient. The liquid pharmaceutical composition of the present invention is in the form of a suspension or a solution.

The pharmaceutically acceptable vehicle of the instant invention may comprise of purified water, one or more suitable organic solvents, and mixtures thereof. The organic solvents may be selected from the group consisting of ethanol, glycerin, propylene glycol, polyethylene glycol, and mixtures thereof. The pharmaceutically acceptable vehicle may optionally have one or more pharmaceutically acceptable excipients.

The term "activation," as used herein means a process which reconstitutes the solid composition with the pharmaceutically acceptable vehicle to form a liquid pharmaceutical composition. The activation can be done by the end-users such as patients or pharmacists or caregiver. The activation process starts by screwing the reservoir.

The term "multi-dose" as used herein, means the liquid pharmaceutical composition is to be administered in multiple doses after reconstitution, over a period of time e.g., for more than seven days, or more than a month, or more than three months.

The term "about" as used herein, refers to any value which lies within the range defined by a variation of up to ±10% of the value.

The term "stable," as used herein, refers to chemical stability, wherein not more than 5% w/w of total related substances are formed on storage at 40° C. and 75% relative humidity (R.H.) or at 25° C. and 60% R.H. for a period of at least three months to the extent necessary for the sale and use of the composition.

The term "pharmaceutically acceptable excipients," as used herein, refers to excipients that are routinely used in pharmaceutical compositions. The pharmaceutically acceptable excipients may comprise glidants, sweeteners, suspending agents, anti-caking agents, wetting agents, preservatives, buffering agents, flavoring agents, anti-oxidants, chelating agents, solutes, and combinations thereof.

The term "extended release," as used herein, refers to a release profile of active ingredient over an extended period of time, e.g., over a period of 0.5, 2, 4, 6, 8, 12, 24 hours, or more.

The term "substantial," as used herein refers to any value which lies within the range as defined by a variation of up to ±15 from the average value.

The term "suspension base," as used herein, refers to a medium which is used to suspend the coated cores of the active ingredient. The suspension base comprises a pharmaceutically acceptable vehicle, one or more osmogents, and pharmaceutically acceptable excipients. The powder for suspension having coated cores of active ingredient of the present invention may be reconstituted with the suspension base having osmogents, pharmaceutically acceptable excipients, and a pharmaceutically acceptable vehicle. Alternatively, osmogents and pharmaceutically acceptable excipients may be mixed with the coated cores of active ingredient which may then be reconstituted with a pharmaceutically acceptable vehicle. The suspension base of the present invention does not include a saturated solution of active ingredient.

The term "inert particle," as used herein, refers to a particle made from a sugar sphere also known as a nonpareil seed, a microcrystalline cellulose sphere, a dibasic calcium phosphate bead, a mannitol bead, a silica bead, a tartaric acid pellet, a wax based pellet, and the like.

The term "Sphericity," as used herein, refers to the closeness of the shape of an object to that of a mathematically perfect sphere. A perfectly spherical particle has a sphericity ($SPHT_3$) value of 1. The cores of active ingredient coated with a release-controlling agent have sphericity ($SPHT_3$) value more than about 0.7 when measured using CamSizer particle analyzer from Retsch Technology.

The term "Angle of repose (AoR)," as used herein, refers to the angle assumed by a cone-like pile of the material relative to a horizontal base upon which it has been poured. The cores of active ingredient coated with a release-controlling agent exhibit an angle of repose less than about 40°.

The term "Hausner Ratio (HR)," as used herein, refers to the unsettled volume divided by the tapped volume (that is the volume after tapping produces no further change in volume), or alternatively the tapped density divided by the bulk density. The cores of active ingredient coated with a release-controlling agent exhibit Hausner ratio less than about 1.25.

The term "Carr's Compressibility Index (CI)," as used herein, can be calculated from the Hausner ratio (HR) as $CI=100\times[1-(1/HR)]$. The cores of active ingredient coated with a release-controlling agent exhibit Carr's Compressibility Index less than about 20.

The term "Desired flowability," as used herein, refers to the uniformity of fill weight of the coated cores. In other words, second chamber after being filled coated cores of the present invention, exhibit weight variation within the range of about ±7.5%.

The term "Sedimentation volume (Suspendibility, F)," as used herein, refers to the ratio of the final or ultimate volume (or height) of the sediment, $V_u$ (or $H_u$) to the original volume (or height) of the suspension, $V_o$, (or $H_o$), before settling. Thus, $F=V_u/V_o$ (or $H_u/H_o$).

The term "Water activity ($a_w$)," as used herein, refers to the measurement of water vapor pressure generated by the free or non-chemically bound water. Compositions with high water activity support growth of microorganisms. One of ways to control microbial contamination is to formulate a low water activity composition. The reconstituted composition of the present invention is characterized by having water activity of suspension base sufficiently low to prevent growth of *Burkholderia cepacia* complex.

The term "High-dose" as used herein, refers to an active ingredient having dose more than or equal to about 250 mg.

The term "Low-dose" as used herein, refers to an active ingredient having dose less than about 250 mg.

The term "Water-soluble" as used herein, refers to an active ingredient which requires less than about 1,000 parts of solvent for dissolution of one part of solute.

The term "Water-insoluble" as used herein, refers to an active ingredient which requires ≥about 1,000 parts of solvent for dissolution of one part of solute.

The term "Substantially impermeable polymeric membrane" as used herein, refers to a polymeric membrane having moisture vapor transmission rate less than about 5.0 g/m²/day.

According to one embodiment of the above aspect, the breakable substantially impermeable polymeric membrane has moisture vapor transmission rate in the range of about 0.8 to about 0.9 g/m²/day.

The average diameter ($D_{50}$) of the coated cores ranges from about 10 μm to about 2000 μm, particularly from about 100 μm to about 1000 μm, and more particularly from about 100 μm to about 500 μm when measured using CamSizer particle analyzer from Retsch Technology. The finer sizes of the cores help in avoiding grittiness in the mouth and are therefore more acceptable.

This dual-chamber pack can be used for a soluble, a water-insoluble, or a poorly-soluble active ingredient. The active ingredient may have a stability problem due to which the active ingredient is reconstituted using a pharmaceutically acceptable vehicle at the time of administration. This dual-chamber pack can be used for active ingredients such as valacyclovir, metformin, azithromycin, cloxacillin, clarithromycin, erythromycin, amoxicillin alone or in combination with clavulanic acid, cefdinir, cefuroxime axetil, cefixime, cefadroxil, cefpodoxime, cefaclor, cefprozil, fluconazole, voriconazole, acarbose, miglitol, voglibose, repaglinide, nateglinide, glibenclamide, glimepride, glipizide, gliclazide, chloropropamide, tolbutamide, phenformin, alogliptin, sitagliptin, linagliptin, saxagliptin, rosiglitazone, pioglitazone, troglitazone, faraglitazar, englitazone, darglitazone, isaglitazone, zorglitazone, liraglutide, muraglitazar, peliglitazar, tesaglitazar, canagliflozin, dapagliflozin, remogliflozin, sergliflozin, verapamil, albuterol, salmeterol, acebutolol, sotalol, penicillamine, norfloxacin, ciprofloxacin, ofloxacin, levofloxacin, moxifloxacin, trovafloxacin, gatifloxacin, tetracycline, demeclocycline hydrochloride, losartan, irbesartan, eprosartan, valsartan, diltiazem, isosorbide mononitrate, ranolazine, propafenone, hydroxyurea, hydrocodone, delavirdine, pentosan polysulfate, abacavir, amantadine, acyclovir, ganciclovir, valganciclovir, saquinavir, indinavir, nelfinavir, lamivudine, didanosine, zidovudine, nabumetone, celecoxib, mefenamic acid, naproxen, propoxyphene, cimetidine, ranitidine, albendazole, mebendazole, thiobendazole, pyrazinamide, praziquantel, chlorpromazine, sumatriptan, bupropion, aminobenzoate, pyridostigmine bromide, potassium chloride, niacin, tocainide, quetiapine, fexofenadine, sertraline, chlorpheniramine, rifampin, methenamine, nefazodone, modafinil, metaxalone, morphine, sevelamer, lithium carbonate, flecainide acetate, simethicone, methyldopa, chlorthiazide, metyrosine, procainamide, entacapone, metoprolol, propanolol hydrochloride, chlorzoxazone, tolmetin, tramadol, bepridil, phenytoin, gabapentin, terbinafine, atorvastatin, doxepine, rifabutin, mesalamine, etidronate, nitrofurantoin, choline magnesium trisalicylate, theophylline, nizatidine, methocarbamol, mycophenolate mofetil, tolcapone, ticlopidine, capecitabine, orlistat, colsevelam, meperidine, hydroxychloroquine, guaifenesin, guanfacine, amiodarone, quinidine, atomoxetine, felbamate, pseudoephedrine, carisoprodol, venlafaxine, etodolac, chondroitin, lansoprazole, pantoprazole, esomeprazole, dexlansoprazole, dexmethylphenidate, methylphenidate, sodium oxybate, valproic acid or its salts, divalproex, topiramate, carbamazepine, oxcarbazepine, isotretinoin, oseltamivir, cholestyramine, nystatin, artemether, lumefantrine, or combination thereof.

The liquid pharmaceutical composition of the present invention may comprise of two or more different active ingredients or incompatible active ingredients.

Suitable film-forming agents include, but not limited to cellulosic polymers e.g., hydroxypropylmethyl cellulose, hydroxypropyl cellulose, polyvinyl acetate, polyvinyl pyrrolidone, acrylic polymers such as these commercially available under the trade mark Eudragit® E and Eudragit® EPO, lipid coating substances such as stearic acid, palmitic acid, and glycerol monostearate; hydrophilic colloids such as alginate, chitosan, carboxymethylcellulose, xanthan gum, carboxy vinyl polymers e.g., Carbomer® 94, polylysine, gelatin; and mixtures thereof.

The ion-exchange resins such as cation- and anion-exchange matrices are well-known in the art. Few exemplary resin particles that can be used according to the invention include, but are not limited to, Dowex® resins and others made by Dow Chemical; Amberlite®, Amberlyst® and other resins made by Rohm and Haas; Indion® resins made by Ion Exchange, Ltd. (India), Diaion® resins by Mitsubishi; Type AG® and other resins by BioRad; Sephadex® and Sepharose® made by Amersham; resins by Lewatit, sold by Fluka; Toyopearl® resins by Toyo Soda; IONAC® and Whatman® resins sold by VWR; and BakerBond® resins sold by J T Baker; resins having polymer backbones comprising styrene-divinyl benzene copolymers and having pendant ammonium or tetraalkyl ammonium functional groups, available from Rohm and Haas, Philadelphia, and sold under the tradename DUOLITE™ AP143.

Suitable suspending agents are selected from the group comprising cellulose derivatives such as co-processed spray dried forms of microcrystalline cellulose and carboxymethyl cellulose sodium, hydroxypropyl cellulose, hydroxyethyl cellulose, hydroxypropylmethyl cellulose, methylcellulose, carboxymethyl cellulose and its salts/derivatives, and microcrystalline cellulose; carbomers; gums such as locust bean gum, xanthan gum, tragacanth gum, arabinogalactan gum, agar gum, gellan gum, guar gum, apricot gum, karaya gum, sterculia gum, acacia gum, gum arabic, and carrageenan; pectin; dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; and mixtures thereof. Co-processed spray dried forms of microcrystalline cellulose and carboxymethyl cellulose sodium have been marketed under the trade names Avicel® RC-501, Avicel® RC-581, Avicel® RC-591, and Avicel® CL-611.

Suitable glidants are selected from the group comprising silica, calcium silicate, magnesium silicate, colloidal silicon dioxide, cornstarch, talc, stearic acid, magnesium stearate, calcium stearate, sodium stearyl fumarate, hydrogenated vegetable oil, and mixtures thereof.

Suitable sweeteners are selected from the group comprising saccharine or its salts such as sodium, potassium, or calcium, cyclamate or its salt, aspartame, alitame, acesulfame or its salt, stevioside, glycyrrhizin or its derivatives, sucralose, and mixtures thereof.

Suitable anti-caking agents are selected from the group comprising colloidal silicon dioxide, tribasic calcium phosphate, powdered cellulose, magnesium trisilicate, starch, and mixtures thereof.

Suitable wetting agents are selected from the group comprising anionic, cationic, nonionic, or zwitterionic surfactants, or combinations thereof. Suitable examples of wetting agents are sodium lauryl sulphate; cetrimide; polyethylene glycols; polyoxyethylene-polyoxypropylene block copolymers such as poloxamers; polyglycerin fatty acid esters such as decaglyceryl monolaurate and decaglyceryl monomyristate; sorbitan fatty acid esters such as sorbitan monostearate; polyoxyethylene sorbitan fatty acid esters such as polyoxyethylene sorbitan monooleate; polyethylene glycol fatty acid esters such as polyoxyethylene monostearate; polyoxyethylene alkyl ethers such as polyoxyethylene lauryl ether; polyoxyethylene castor oil; and mixtures thereof.

Suitable preservatives are selected from the group comprising parabens such as methyl paraben and propyl paraben; sodium benzoate; and mixtures thereof.

Suitable buffering agents are selected from the group comprising citric acid, sodium citrate, sodium phosphate, potassium citrate, acetate buffer, and mixtures thereof.

Suitable flavoring agents are selected from the group consisting of peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, salvia, aloe vera balsam, spearmint, eucalyptus, and combinations thereof.

Suitable anti-oxidants are selected from the group comprising butylated hydroxytoluene (BHT), butylated hydroxyanisole (BHA), sodium metabisulfite, ascorbic acid, propyl gallate, thiourea, tocopherols, beta-carotene, and mixtures thereof.

Suitable chelating agents are selected from the group comprising ethylenediamine tetraacetic acid or derivatives/salts thereof, e.g., disodium edetate; dihydroxyethyl glycine; glucamine; acids, e.g., citric acid, tartaric acid, gluconic acid, and phosphoric acid; and mixtures thereof.

The term "solute," as used herein, refers to pharmaceutically acceptable inert agents that have high affinity for the pharmaceutically acceptable vehicle. The solutes generates hypertonic conditions leading to high osmolality and thus prevents the leaching of the active ingredient from the coated cores. The solutes can be present in the pharmaceutically acceptable vehicle or in the solid composition or both. Suitable solutes are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide; xanthan gum; hydroxypropylmethyl cellulose; and mixtures thereof. Particularly, the solutes used are xylitol, mannitol, glucose, lactose, sucrose, and sodium chloride.

The cores of the present invention comprising the active ingredient can be prepared by any method known in the art, e.g., extrusion-spheronoization, wet granulation, dry granulation, hot-melt extrusion granulation, spray drying, and spray congealing. Alternatively, the active ingredient can be layered onto an inert particle to form the core. Further, the active ingredient particles can be directly coated with a film forming layer to form the microparticles or microcapsules. The microparticles or microcapsules can be prepared by a process of homogenization, solvent evaporation, coacervation phase separation, spray drying, spray congealing, polymer precipitation, or supercritical fluid extraction. The ion-exchange resins comprise loading a plurality of the resin particles with the active ingredient to form drug-resin cores. Methods of loading active ingredients onto the resin particles are generally known in the art.

The first chamber includes a container which is in the form of a glass or a plastic or a metallic bottle. The reservoir of the second chamber can be made of a plastic, a metal or a glass; particularly the reservoir is a plastic bottle. The reservoir of the second chamber may additionally have a slippery coating or mold polishing. This coating or polishing will help to improve the flow characteristics of the solid composition during activation.

The dual-chamber pack is suitable for incorporating solid composition in a volume of greater than about 40 cc. In the dual-chamber pack, the plunger is opened at both the ends. The biphasic connector comprises of cross bridges to give the strength. The bridges can be tapered at the edges to avoid any powder deposit. Further, the reservoir can have serrations to have better grip for the end-users. The biphasic connector have a tamper-evident band on the side connected to the container of the first chamber which is removed first to start the activation process. The biphasic connector is having grooves on other side for locking with the reservoir. On this side, there would be instructions for the end-users regarding direction of the rotation such as clockwise rotation for activating the pack.

The term "tamper-evident band," as used herein, refers to a band attached co-axially to the biphasic connector. The band breaks easily on pulling apart. The tamper-evident band ensures the overall integrity of the product until activation.

The plunger of the instant invention can comprise of one or more sharp projections with an essential continuous blunt area. In particular, the plunger comprise of one sharp projection with an essential continuous blunt area. Alternatively, the plunger can have a single continuous projection with a remaining continuous blunt area which can be called as a flute shaped plunger. The plunger can further have one or more grooves. The body of the plunger can be in the form of a cylinder or a funnel. The funnel shaped plunger provides additional capacity for storing high-dose active ingredients or active ingredients required for chronic administration.

The plunger used in the instant invention ensures that the breakable polymeric membrane remains attached to the plug during activation. The plug and the plunger may be made up of a polymeric material selected from the group comprising polyolefin, polyethylene, polypropylene, polyvinyl chloride, cyclic olefin polymer, cyclic olefin co-polymer, polyethylene terephthalate, polyethylene terephthalate-G, polypropylene, and polycarbonate. Particularly, the plug and the plunger are made up of polyethylene. More particularly, the plug and the plunger are made up of linear low density polyethylene (LLDPE).

The compositions of the first and second chambers of the container are separated by a polymeric breakable membrane of the plug. The plunger used in the instant invention helps to rupture the breakable polymeric membrane upon the application of pressure by a screw-based mechanism. When pressure is applied on the reservoir, the breakable polymeric membrane is ruptured by the plunger. The intact polymeric membrane remains attached to the circumference of the plug. In cases, where a bottle liner exists between the first and the second chambers, the plunger would break the bottle liner in the same manner as it ruptures the breakable polymeric membrane. The unabridged part of the bottle liner remains attached to the opening of the container. The plug with the breakable polymeric membrane prevents moisture permeation from the first chamber into the second chamber.

The material used for making the plug may also include moisture barrier additives selected from the plastic additive group comprising of monomers and co-polymers that get activated through polymerization process to form an effective organic chemical. The moisture barrier additives used in the present invention may include any material that prevent moisture permeation. The moisture barrier additives may be present in the form of a layer inside the plug. The moisture barrier additives may be present in an amount of 0.1% to 10% w/w, in particularly, 0.5% to 5% w/w based on total weight of the material used for making plug.

The material used for making the reservoir may also include the moisture barrier additives. The moisture barrier additives may be present in the form of a layer inside the reservoir.

The moisture permeation test was carried out on dual chamber packs with moisture barrier additives and without moisture barrier additives as per USP (37)-671 Containers Performance Testing. The moisture barrier additives used in the present invention improve the moisture barrier properties by up to 50%. In particular, the moisture barrier additives improves the moisture barrier properties by up to 30%.

The use of moisture barrier additives thus help to prevent the moisture permeation from the pharmaceutically acceptable vehicle into the solid composition comprising the active ingredient during storage. The active ingredient, particularly moisture-sensitive active ingredients thus remains stable during storage.

The invention may be further illustrated by the following example, which is for illustrative purposes only and should not be construed as limiting the scope of the invention in any way.

EXAMPLES

Example 1

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 68.31 |
| Dibutyl sebacate | 1.69 |
| Acetone | q.s. |
| Purified water | q.s. |
| Total Weight of Extended Release Beads | 210.00 mg |
| Suspension Base | |
| Metformin hydrochloride | 20.00 |
| Xylitol | 450.00 |
| Microcrystalline cellulose - sodium carboxymethyl cellulose (Avicel ® CL-611) | 20.00 |
| Xanthan gum | 1.50 |
| Methyl paraben | 1.80 |
| Propyl paraben | 0.20 |
| Strawberry flavor | 2.00 |
| Sucralose | 0.50 |
| Colloidal silicon dioxide | 3.50 |
| Purified water | 472.00 mg |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3 and dried to form a powder for suspension.
5. Purified water was heated to dissolve methyl paraben and propyl paraben.
6. Metformin hydrochloride, xylitol, microcrystalline cellulose-sodium carboxymethyl cellulose, xanthan gum, strawberry flavor, sucralose, and colloidal silicon dioxide were mixed in the solution of step 5 to form a suspension base.
7. The powder for suspension of step 4 was filled in the second chamber of a drug delivery device.
8. The suspension base of step 6 was filled in a container of a first chamber of a drug delivery device.
9. The two chambers were assembled and the drug delivery device was activated to form the extended release liquid composition when required.

In-Vitro Studies of Extended Release Reconstituted Powder for Suspension

The extended release reconstituted powder for suspension prepared as per Example 1 (for a dose equivalent to 750 mg of metformin hydrochloride) was stored at room temperature for 120 days. The in-vitro dissolution was determined at 0, 45, 90, and 120 days using USP type II apparatus at 100 rpm, in 1000 mL of phosphate buffer with pH 6.8 at 37° C. The results of the release studies are represented in Table 1.

TABLE 1

Percentage (%) of the In-Vitro Metformin Release in USP Type II Apparatus (Media: Phosphate Buffer, pH 6.8, 1000 mL, and 100 rpm)

| Time (hours) | Number of Days | | | |
|---|---|---|---|---|
| | 0 | 45 | 90 | 120 |
| | Percentage of Metformin Release | | | |
| 0.5 | 20 | 21 | 20 | 21 |
| 1 | 27 | 25 | 27 | 25 |
| 2 | 55 | 52 | 55 | 52 |
| 3 | 74 | 72 | 74 | 72 |
| 4 | 83 | 81 | 83 | 81 |
| 5 | 85 | 86 | 85 | 86 |
| 6 | 87 | 90 | 87 | 90 |
| 8 | 91 | 94 | 91 | 94 |
| 10 | 93 | 96 | 93 | 96 |
| 12 | 94 | 97 | 94 | 97 |

From the above in-vitro release data, it is evident that the extended release reconstituted powder for suspension prepared according to Example 1 provides the substantially similar in-vitro metformin release for 120 days.

The drug delivery device was kept for 1 month at accelerated conditions i.e., 40° C./75% R.H. After 1 month, the drug delivery device was activated to form an extended release reconstituted powder for suspension which was kept for 120 days at room temperature. The in-vitro dissolution was determined at 0, 45, 90, and 120 days using USP type II apparatus at 100 rpm, in 1000 mL of phosphate buffer with pH 6.8 at 37° C. The results of the release studies are represented in Table 2.

TABLE 2

Percentage (%) of the In-Vitro Metformin Release in USP Type II Apparatus (Media: Phosphate Buffer, pH 6.8, 1000 mL, and 100 rpm)

| Time (hours) | Number of Days | | | |
|---|---|---|---|---|
| | 0 | 45 | 90 | 120 |
| | Percentage of Metformin Release | | | |
| 0.5 | 21 | 21 | 21 | 20 |
| 1 | 27 | 25 | 26 | 26 |
| 2 | 56 | 55 | 52 | 54 |
| 3 | 74 | 74 | 76 | 72 |
| 4 | 83 | 81 | 82 | 81 |
| 10 | 96 | 96 | 97 | 94 |

The drug delivery device was kept for 3 months at accelerated conditions i.e., 40° C./75% R.H. After 3 months, the drug delivery device was activated to form an extended release reconstituted powder for suspension which was kept for 120 days at room temperature. The in-vitro dissolution was determined at 0, 45, 90, and 120 days using USP type II apparatus at 100 rpm, in 1000 mL of phosphate buffer with pH 6.8 at 37° C. The results of the release studies are represented in Table 3.

TABLE 3

Percentage (%) of the In-Vitro Metformin Release in USP Type II Apparatus (Media: Phosphate Buffer, pH 6.8, 1000 mL, and 100 rpm)

| Time (hours) | Number of Days | | | |
|---|---|---|---|---|
| | 0 | 45 | 90 | 120 |
| | Percentage of Metformin Release | | | |
| 0.5 | 21 | 21 | 21 | 20 |
| 1 | 26 | 25 | 25 | 26 |
| 2 | 55 | 53 | 53 | 60 |
| 3 | 75 | 72 | 72 | 73 |
| 4 | 80 | 80 | 79 | 82 |
| 10 | 95 | 92 | 96 | 97 |

The drug delivery device was kept for 6 months at accelerated conditions i.e., 40° C./75% R.H. After 6 months, the drug delivery device was activated to form an extended release reconstituted powder for suspension which was kept for 120 days at room temperature. The in-vitro dissolution was determined at 0, 45, 90, and 120 days using USP type II apparatus at 100 rpm, in 1000 mL of phosphate buffer with pH 6.8 at 37° C. The results of the release studies are represented in Table 4.

TABLE 4

Percentage (%) of the In-Vitro Metformin Release in USP Type II Apparatus (Media: Phosphate Buffer, pH 6.8, 1000 mL, and 100 rpm)

| Time (hours) | Number of Days | | | |
|---|---|---|---|---|
| | 0 | 45 | 90 | 120 |
| | Percentage of Metformin Release | | | |
| 0.5 | 18 | 19 | 19 | 20 |
| 1 | 23 | 24 | 25 | 28 |
| 2 | 50 | 56 | 54 | 57 |
| 3 | 70 | 71 | 74 | 73 |
| 4 | 78 | 80 | 79 | 81 |
| 10 | 95 | 95 | 94 | 94 |

From the above data, it is clear that the powder for suspension and suspension base stored in the drug delivery device of the instant invention at accelerated conditions for 1 month, 3 months and 6 months, upon activation of the drug delivery device forms extended release reconstituted powder for suspension which when stored for 120 days at room temperature provides substantially similar in-vitro metformin release.

Stability Data of Extended Release Reconstituted Powder for Suspension

The related substances for the extended release reconstituted powder for suspension prepared as per Example 1 were determined at 0 day and after storage at room temperature for 45 and 120 days. The powder for suspension and suspension base was stored in the drug delivery device for one month and for three months at 40° C./75% R.H. After one month or three months, the drug delivery device was activated to form an extended release reconstituted powder for suspension and then related substances were determined at 0 day and after storage at room temperature for 45 days and 120 days.

The related substances of metformin was determined by HPLC method. The results are shown in Table 5.

TABLE 5

Stability Data for Metformin in the Drug Delivery Device

| Related Substances (% w/w) | Initial | | | 1 month (40° C./75% R.H) | | | 3 month (40° C./75% R.H) | |
|---|---|---|---|---|---|---|---|---|
| | 0 day | 45 days | 120 days | 0 day | 45 days | 120 days | 0 day | 45 days |
| Cyanoguanidine | BLQ | 0.001 | 0.00072 | 0.001 | 0.001 | 0.001 | 0.001 | 0.001 |
| Highest unknown impurity | 0.05 | 0.05 | 0.04 | 0.05 | 0.04 | 0.04 | 0.05 | 0.04 |
| Total impurities | 0.05 | 0.05 | 0.04 | 0.05 | 0.04 | 0.04 | 0.09 | 0.04 |

*BLQ: Below limit of Quantification

It is evident from the above data that the extended release reconstituted powder for suspension prepared as per Example 1 remains stable even after storing at accelerated conditions for 3 months.

Antimicrobial Efficacy Test of Extended Release Reconstituted Powder for Suspension The powder for suspension and suspension base prepared as per Example 1 was stored in the drug delivery device for twenty four months at 25° C./60% R.H. After twenty four months, the drug delivery device was activated to form an extended release reconstituted suspension which was tested for antimicrobial efficacy as per USP and also by inoculating with *Burkholderia cepacia* complex. Extended release reconstituted suspension prepared after activation of the drug delivery device was found to comply with the Antimicrobial Efficacy Test as per USP. Growth of *Burkholderia cepacia* complex was found to be inhibited in the reconstituted suspension.

It is evident from the above test that microbial growth was not promoted in the extended release reconstituted powder for suspension composition prepared after activation of the drug delivery device.

In-Vitro Studies of Extended Release Coated Cores

Extended release coated cores of Example 1 (step 4) were stored in the drug delivery device and kept for 1, 3 and 6 months at accelerated conditions i.e., 40° C./75% RH. Coated cores were then subjected to determination of water content after 1, 3 and 6 months of storage at 40° C./75% RH using Karl Fischer Apparatus. The results of the water content determination are represented in Table 5A.

TABLE 5A

Water Content of Extended Release Coated Cores

| Time Period | Water Content |
|---|---|
| Initial | 1.08 |
| 1 month (40° C./75% RH) | 1.56 |
| 3 month (40° C./75% RH) | 0.73 |
| 6 month (40° C./75% RH) | 1.79 |

From the above data, it is evident that there was no change in water content of the extended release coated cores prepared according to Example 1 (step 4) after six months of storage at 40° C./75% RH.

Example 2

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 75.14 |
| Dibutyl sebacate | 1.856 |
| Acetone | q.s. |
| Purified water | q.s. |
| Total Weight of Extended Release Beads | 217.00 mg |
| Lubrication | |
| Magnesium stearate | 1.500 |
| Suspension Base | |
| Metformin hydrochloride | 20.00 |
| Xylitol | 450.00 |
| Microcrystalline cellulose - sodium carboxymethyl cellulose (Avicel® CL-611) | 20.00 |
| Xanthan gum | 1.50 |
| Methyl paraben | 1.80 |
| Propyl paraben | 0.20 |
| Strawberry flavor | 1.50 |
| Sucralose | 0.50 |
| Colloidal silicon dioxide | 3.50 |
| Purified water | 465.5 |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3 and dried to form extended release beads.
5. The extended release beads of step 4 were lubricated with Magnesium stearate to form powder for suspension.
6. Purified water was heated to dissolve methyl paraben and propyl paraben.
7. Metformin hydrochloride, xylitol, microcrystalline cellulose-sodium carboxymethyl cellulose, xanthan gum, strawberry flavor, sucralose, and colloidal silicon dioxide were mixed in the solution of step 6 to form a suspension base.
8. The powder for suspension of step 5 was filled in the second chamber of a drug delivery device.
9. The suspension base of step 7 was filled in a container of a first chamber of a drug delivery device.

10. The two chambers were assembled and activated to form the extended release liquid composition when required.

Flow Properties of Extended Release Coated Cores

Extended release coated cores of Example 2 (step 5) were evaluated for the following parameters:

Angle of Repose (AoR)—Angle of Repose was determined by passing the extended release coated cores through Enar Reposograph to make the cone. Then, height of the cone (h) thus formed and the radius (r) of the base of the cone were measured. Angle of repose (θ) was calculated as follows:

$$\theta = \tan^{-1}(h/r)$$

Hausner ratio (HR)—Hausner ratio was determined by dividing the tapped density ($\rho_{tap}$) by the bulk density ($\rho_{bulk}$).

Carr's Compressibility Index (CI)—Carr's Compressibility Index was determined from the Hausner ratio (HR) as $CI = 100 \times [1-(1/HR)]$

TABLE 6

Flow Property of Extended Release Coated Cores of Metformin Hydrochloride

| Flow Property Parameter | Observed Value | Flow Character |
|---|---|---|
| Angle of Repose (°) | 25.87 | Excellent |
| Carr's Compressibility Index (%) | 7.32 | Excellent |
| Hausner ratio | 1.08 | Excellent |

The powder for suspension was found to have desired flowability.

In-Vitro Studies of Extended Release Coated Cores

Extended release coated cores of Example 2 (step 5) were stored in the drug delivery device and kept for 6 month at accelerated conditions i.e., 40° C./75% RH Coated cores were then subjected to in-vitro dissolution testing after six months of storage at 40° C./75% RH using USP type II apparatus at 100 rpm, in 1000 mL of phosphate buffer with pH 6.8 at 37° C. The results of the release studies are represented in Table 7.

TABLE 7

Percentage (%) of the In-Vitro Metformin Release from Extended Release Coated Cores in USP Type II Apparatus (Media: Phosphate Buffer, pH 6.8, 1000 mL, 100 rpm)

| | Time Period | |
|---|---|---|
| Time (hours) | Initial | After six months at 40° C./75% RH |
| | Percentage of Metformin Release | |
| 0.5 | 1 | 0 |
| 2 | 46 | 43 |
| 12 | 95 | 93 |

From the above in-vitro release data, it is evident that the extended release coated cores prepared according to Example 2 (step 5) provide substantially similar in-vitro metformin release after six months of storage at 40° C./75% RH. Thus, the extended release coated cores prepared as per the present invention are stable when stored in the second chamber of the drug delivery device for at least six months under accelerated conditions.

Uniformity of Fill Weight of Extended Release Coated Cores

Extended release coated cores prepared according to Example 2 (step 5) were filled into the second chamber of drug delivery devices. A total of 960 drug delivery devices were filled. Target fill weight was 106.995 g. Average weight was found to be 107.52 g, minimum observed fill weight was 106.14 g, maximum fill weight was 107.95 g and % RSD was found to be 0.25. Entire batch was filled within ±7.5% of the target weight.

Thus, % weight variation with respect to target fill weight of extended release coated cores was found to be within the range of about ±7.5%.

In-Vitro Studies of Extended Release Reconstituted Powder for Suspension

The extended release reconstituted powder for suspension prepared as per Example 2 (was stored at room temperature for 100 days. The in-vitro dissolution was determined at 0, 45, and 100 days using USP type II apparatus at 100 rpm, in 1000 mL of phosphate buffer with pH 6.8 at 37° C. The results of the release studies are represented in Table 8.

TABLE 8

Percentage (%) of the In-Vitro Metformin Release in USP Type II Apparatus (Media: Phosphate Buffer, pH 6.8, 1000 mL, and 100 rpm)

| | Number of Days | | |
|---|---|---|---|
| | 0 | 45 | 100 |
| Time (hours) | Percentage of Metformin Release | | |
| 0.5 | 20 | 21 | 21 |
| 1 | 24 | 26 | 27 |
| 2 | 58 | 60 | 61 |
| 3 | 78 | 75 | 79 |
| 4 | 86 | 82 | 86 |
| 12 | 99 | 94 | 100 |

From the above in-vitro release data, it is evident that the extended release reconstituted powder for suspension prepared according to Example 2 provides the substantially similar in-vitro metformin release for 100 days.

The drug delivery device was kept for 1 month at accelerated conditions i.e., 40° C./75% R.H. After 1 month, the drug delivery device was activated to form an extended release reconstituted powder for suspension which was kept for 100 days at room temperature. The in-vitro dissolution was determined at 0, 45, and 100 days using USP type II apparatus at 100 rpm, in 1000 mL of phosphate buffer with pH 6.8 at 37° C. The results of the release studies are represented in Table 9.

TABLE 9

Percentage (%) of the In-Vitro Metformin Release in USP Type II Apparatus (Media: Phosphate Buffer, pH 6.8, 1000 mL, and 100 rpm)

| | Number of Days | | |
|---|---|---|---|
| | 0 | 45 | 100 |
| Time (hours) | Percentage of Metformin Release | | |
| 0.5 | 19 | 19 | 19 |
| 2 | 55 | 54 | 58 |
| 12 | 91 | 92 | 97 |

The drug delivery device was kept for 3 months at accelerated conditions i.e., 40° C./75% R.H. After 3 months, the drug delivery device was activated to form an extended release reconstituted powder for suspension which was kept for 100 days at room temperature. The in-vitro dissolution was determined at 0 and 100 days using USP type II apparatus at 100 rpm, in 1000 mL of phosphate buffer with pH 6.8 at 37° C. The results of the release studies are represented in Table 10.

TABLE 10

Percentage (%) of the In-Vitro Metformin Release in USP Type II
Apparatus (Media: Phosphate Buffer, pH 6.8, 1000 mL, and 100 rpm)

| Time (hours) | Number of Days | |
|---|---|---|
| | 0 | 100 |
| | Percentage of Metformin Release | |
| 0.5 | 19 | 19 |
| 2 | 57 | 60 |
| 12 | 97 | 95 |

The drug delivery device was kept for 6 months at accelerated conditions i.e., 40° C./75% R.H. After 6 months, the drug delivery device was activated to form an extended release reconstituted powder for suspension which was kept for 100 days at room temperature. The in-vitro dissolution was determined at 0 and 100 days using USP type II apparatus at 100 rpm, in 1000 mL of phosphate buffer with pH 6.8 at 37° C. The results of the release studies are represented in Table 11.

TABLE 11

Percentage (%) of the In-Vitro Metformin Release in USP Type II
Apparatus (Media: Phosphate Buffer, pH 6.8, 1000 mL, and 100 rpm)

| Time (hours) | Number of Days | |
|---|---|---|
| | 0 | 100 |
| | Percentage of Metformin Release | |
| 0.5 | 19 | 19 |
| 2 | 59 | 60 |
| 12 | 96 | 94 |

From the above data, it is clear that the powder for suspension and suspension base stored in the drug delivery device of the instant invention at accelerated conditions for 1 month, 3 months and 6 months, upon activation of the drug delivery device forms extended release reconstituted powder for suspension which when stored for at least 100 days at room temperature provides substantially similar in-vitro metformin release.

Example 3

| Ingredients | Quantity (mg/5 mL) | |
|---|---|---|
| | For 228.5 mg strength | For 457 mg strength |
| Solid composition | | |
| Amoxicillin Trihydrate | 238.15 | 476.30 |
| Potassium Clavulanate + Silicon dioxide (1:1) | 77.63 | 155.25 |
| Colloidal anhydrous silica | 10.00 | 10.00 |
| Silicon dioxide | 126.22 | 10.45 |
| Xanthan gum | 10.00 | 10.00 |
| Monosodium citrate | 6.00 | 6.00 |
| Sodium citrate | 2.00 | 2.00 |
| Aspartame | 10.00 | 10.00 |
| Strawberry flavor | 20.00 | 20.00 |
| Total Fill Weight | 500.00 | 700.00 |
| Suspension Base | | |
| Sodium Benzoate | 10.00 | 10.00 |
| Purified water | q.s. to 5 mL | q.s. to 5 mL |

Procedure:
1. Amoxicillin was dried at 45-55° C. in a tray drier.
2. Xanthan gum, Strawberry flavor, Sodium Citrate, Monosodium citrate, Aspartame and Colloidal anhydrous silica were dried at 75-80° C.
3. Dried Monosodium citrate and Sodium citrate were sifted through a suitable sieve.
4. Strawberry flavor, Xanthan gum, Aspartame and Silicon dioxide were sifted along with blend from step 1 using a suitable sieve.
5. Amoxicillin Trihydrate, Potassium Clavulanate and Colloidal anhydrous silica were sifted along with blend from step 2 using a suitable sieve.
6. The material from step 3 was blended in low shear blender for 30 to 45 minutes.
7. The blend from step 4 was filled in the second chamber of the drug delivery device.
8. Sodium Benzoate was dissolved in Purified water to form the vehicle.
9. Vehicle of step 6 was filled in the first chamber of the drug delivery device.
10. The two chambers were assembled and the device was activated to form the immediate release liquid composition when required.

Stability Data of Immediate Release Reconstituted Powder for Suspension

The related substances for the immediate release reconstituted powder for suspension prepared as per Example 3 were determined at 0 day and the powder for suspension was stored in the second chamber and suspension base was stored in the first chamber of the drug delivery device for one month and for three months at 40° C./75% R.H. After one month or three months, the device was activated to form an immediate release reconstituted powder for suspension and then related substances were determined.

The related substances were determined by HPLC method. The results are shown in Table 12.

TABLE 12

Stability Data for Amoxicillin in the Amoxicillin and Clavulanic Acid
Immediate Release Reconstituted Powder for Suspension in the Drug Delivery Device

| Related Substances (% w/w) | 228.5 mg/5 mL | | | 457 mg/5 mL | | |
|---|---|---|---|---|---|---|
| | Initial | 1 month (40° C./75% R.H) | 3 month (40° C./75% R.H) | Initial | 1 month (40° C./75% R.H) | 3 month (40° C./75% R.H) |
| Amoxicilloic acid-1 | 0.007 | 0.009 | 0.03 | 0.01 | 0.01 | 0.02 |
| Amoxicilloic acid-2 | 0.06 | 0.07 | 0.08 | 0.04 | 0.05 | 0.05 |

TABLE 12-continued

Stability Data for Amoxicillin in the Amoxicillin and Clavulanic Acid
Immediate Release Reconstituted Powder for Suspension in the Drug Delivery Device

| Related Substances (% w/w) | 228.5 mg/5 mL | | | 457 mg/5 mL | | |
|---|---|---|---|---|---|---|
| | Initial | 1 month (40° C./75% R.H) | 3 month (40° C./75% R.H) | Initial | 1 month (40° C./75% R.H) | 3 month (40° C./75% R.H) |
| Amoxilloic acid-1 | 0.008 | 0.022 | 0.05 | ND | ND | 0.03 |
| Amoxilloic acid-2 | 0.004 | 0.018 | 0.03 | 0.004 | 0.021 | 0.02 |
| Diketopiperazine-1 | 0.01 | 0.01 | 0.03 | 0.01 | 0.03 | ND |
| Diketopiperazine-2 | ND | ND | ND | ND | 0.01 | ND |
| 2-hydroxy-3-(4-hydroxyphenyl)-pyrazine | ND | ND | ND | ND | 0.03 | ND |
| Amoxicillin dimer | 0.20 | 0.27 | 0.25 | 0.08 | 0.15 | 0.12 |
| Amoxicillin trimer | 0.006 | ND | 0.01 | 0.01 | ND | ND |
| Highest unknown impurity | 0.05 | 0.23 | 0.03 | 0.04 | 0.10 | 0.08 |
| Total Unknown impurity | 0.32 | 0.37 | 0.15 | 0.17 | 0.26 | 0.19 |
| Total Related Substances | 0.62 | 0.77 | 0.63 | 0.33 | 0.56 | 0.44 |

*ND: Not Detectable

It is evident from the above data that the immediate release reconstituted powder for suspension prepared as per Example 3 remains stable even after storing at accelerated conditions for 3 months.

We claim:

1. A drug delivery device for the in situ preparation of an extended release oral suspension upon activation of the device, the device comprising:
    a) a first chamber comprising a suspension base;
    b) a second chamber comprising a solid composition comprising cores of active ingredient coated with a release controlling agent to form coated cores; and
    c) a breakable substantially impermeable polymeric membrane separating first and second chamber
wherein, the substantially impermeable polymeric membrane is made up of a polymeric material selected from the group consisting of polyethylene (PE), low density polyethylene (LDPE), linear low density polyethylene (LLDPE), high density polyethylene (HDPE) and high barrier grade PE, has a thickness not less than 0.10 mm and a moisture vapor transmission rate less than about 5.0 g/m$^2$/day; and wherein, the solid composition remains stable when stored in the drug delivery device at 40° C./75% RH for at least three months.

2. The drug delivery device of claim 1, wherein the breakable substantially impermeable polymeric membrane prevents intimate contact between the contents of first and second chamber before activation.

3. The drug delivery device of claim 1, wherein the second chamber comprises a plunger for storing the solid composition and a plug fitted with the breakable substantially impermeable polymeric membrane.

4. The drug delivery device of claim 3, wherein after activation of the device, not more than 50% of the circumference of the breakable substantially impermeable polymeric membrane remains attached to the plug to allow free flow of the coated cores from second chamber to first chamber.

5. The drug delivery device of claim 3, wherein the plunger comprises one or more sharp projections with an essential continuous blunt area at an angle of not more than 60°.

* * * * *